US 8,162,949 B2

(12) United States Patent
Duggineni et al.

(10) Patent No.: US 8,162,949 B2
(45) Date of Patent: Apr. 24, 2012

(54) TIBIAL RESECTION GUIDE

(75) Inventors: Rajesh V. Duggineni, Warsaw, IN (US); David Wycliffe Murray, Oxford (GB)

(73) Assignee: Biomet Manufacturing Corp., Warsaw, IN (US)

( * ) Notice: Subject to any disclaimer, the term of this patent is extended or adjusted under 35 U.S.C. 154(b) by 1038 days.

(21) Appl. No.: 12/106,773

(22) Filed: Apr. 21, 2008

(65) Prior Publication Data
US 2009/0264890 A1 Oct. 22, 2009

(51) Int. Cl.
*A61B 17/15* (2006.01)
*A61B 17/56* (2006.01)

(52) U.S. Cl. ....................................... 606/88

(58) Field of Classification Search .................. 606/88, 606/102
See application file for complete search history.

(56) References Cited

U.S. PATENT DOCUMENTS
7,235,080 B2    6/2007  Hodorek
2008/0027452 A1*  1/2008  Sheffer et al. .................. 606/89

FOREIGN PATENT DOCUMENTS
WO   WO-2006087535   8/2006
WO   WO-2006123120   11/2006
* cited by examiner

*Primary Examiner* — Bruce E Snow
*Assistant Examiner* — Melissa Hoban
(74) *Attorney, Agent, or Firm* — Harness, Dickey

(57) ABSTRACT

A tibial resection guide. The tibial resection guide includes a support member having a longitudinal shaft, and a referencing guide coupled to the longitudinal shaft, the referencing guide defining a referencing slot. The tibial resection guide can also include a cutting guide coupled to the longitudinal shaft, the cutting guide defining a cutting slot, the cutting slot positioned at a fixed distance from the referencing slot, and an adjustment mechanism operable to move the referencing guide and the cutting guide along the longitudinal shaft without changing the fixed distance.

20 Claims, 15 Drawing Sheets

TIBIAL RESECTION GUIDE

During knee joint replacement surgery, a portion or the entire tibial plateau may be resected at a specific level and specific angle. Various resection instruments are known for guiding the placement of the bone cuts.

The present teachings provide a tibial resection guide that references the posterior femoral condyles and includes swiveling cutting guide.

SUMMARY

The present teachings provide a tibial resection guide. In one aspect, the tibial resection guide includes a support member having a longitudinal shaft, and a referencing guide coupled to the longitudinal shaft, the referencing guide defining a referencing slot. The tibial resection guide can also include a cutting guide coupled to the longitudinal shaft, the cutting guide defining a cutting slot, the cutting slot positioned at a fixed distance from the referencing slot. The tibial resection guide can further include an adjustment mechanism operable to move the referencing guide and the cutting guide along the longitudinal shaft without changing the fixed distance.

In another aspect the tibial resection guide includes a support member having a longitudinal shaft, and a referencing guide coupled to the longitudinal shaft, the referencing guide integrally forming a stylus arm for engaging the posterior femoral condyles. The tibial resection guide can also include a cutting guide coupled to the longitudinal shaft, the cutting guide defining a cutting slot, the cutting slot positioned at a fixed distance from the stylus arm. The tibial resection guide can further include an adjustment mechanism operable to move the referencing guide and the cutting guide along the longitudinal shaft without changing the fixed distance.

In another aspect, the tibial resection guide includes a support member including a longitudinal shaft; and a referencing guide coupled to the longitudinal shaft, the referencing guide defining a referencing slot, the referencing guide independently rotatable about the longitudinal shaft. The tibial resection guide can also include a first guide portion coupled to the longitudinal shaft and independently rotatable about the longitudinal shaft; a second guide portion coupled to the longitudinal shaft and independently rotatable about the longitudinal shaft, and an adjustment mechanism operable to move the referencing guide and the first and second guide portions along the longitudinal shaft.

The present teachings also provide a method of making a tibial resection. The method includes attaching a tibial resection guide to the tibia; rotating a referencing guide about a shaft of the tibial resection guide to a position adjacent the posterior femoral condyles, adjusting the referencing guide relative to the femoral condyles, passing a referencing stylus member through a referencing slot of the referencing guide, rotating a cutting guide about the shaft of the tibial resection guide toward the tibia, and making a tibial resection cut.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

The following description is merely exemplary in nature and is in no way intended to limit the present teachings, applications, or uses.

Figure 1:
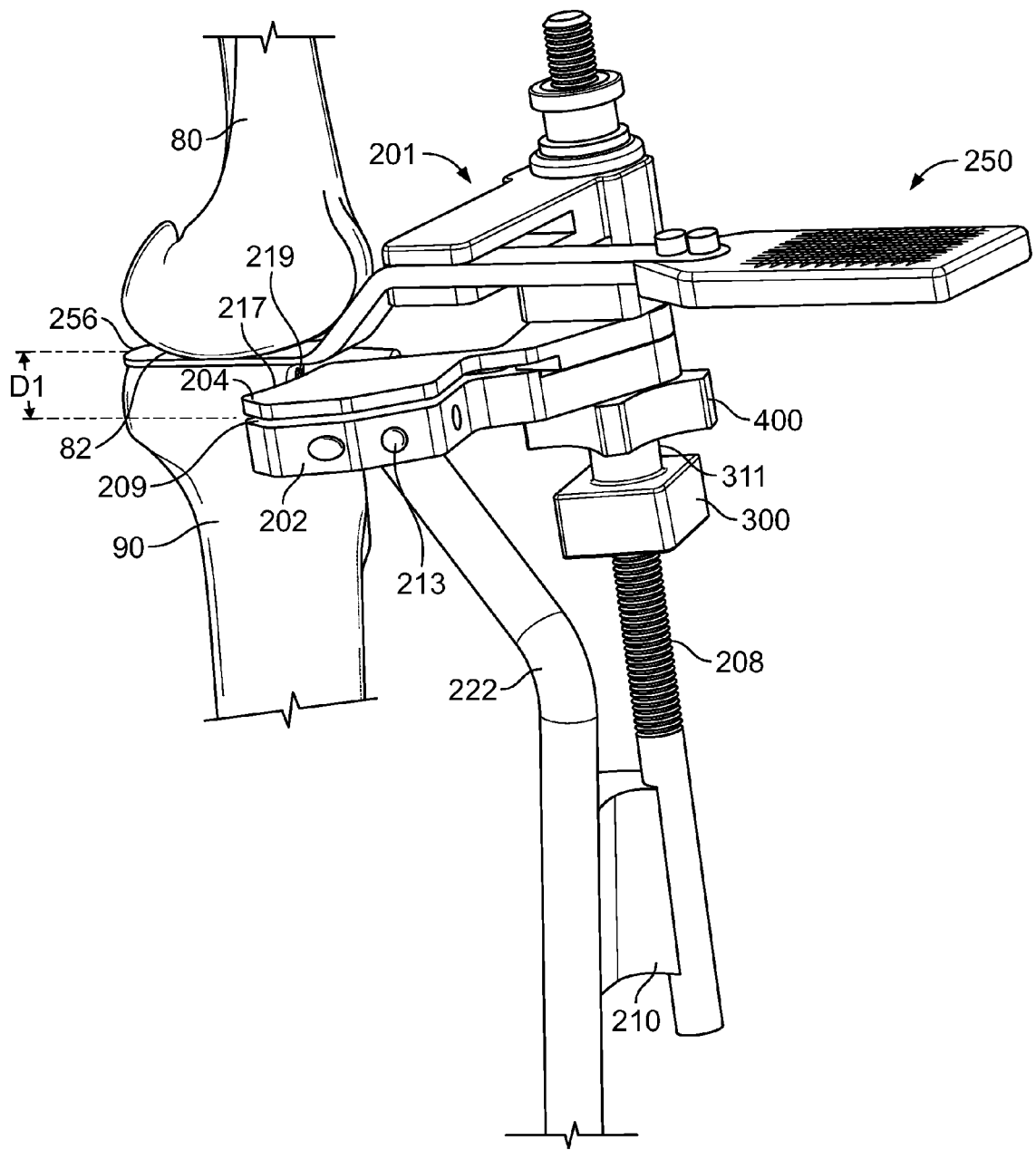
FIG. 1 is an environmental perspective view of a tibial resection guide positioned relative to a knee in extension according to the present teachings.
Figure 2:
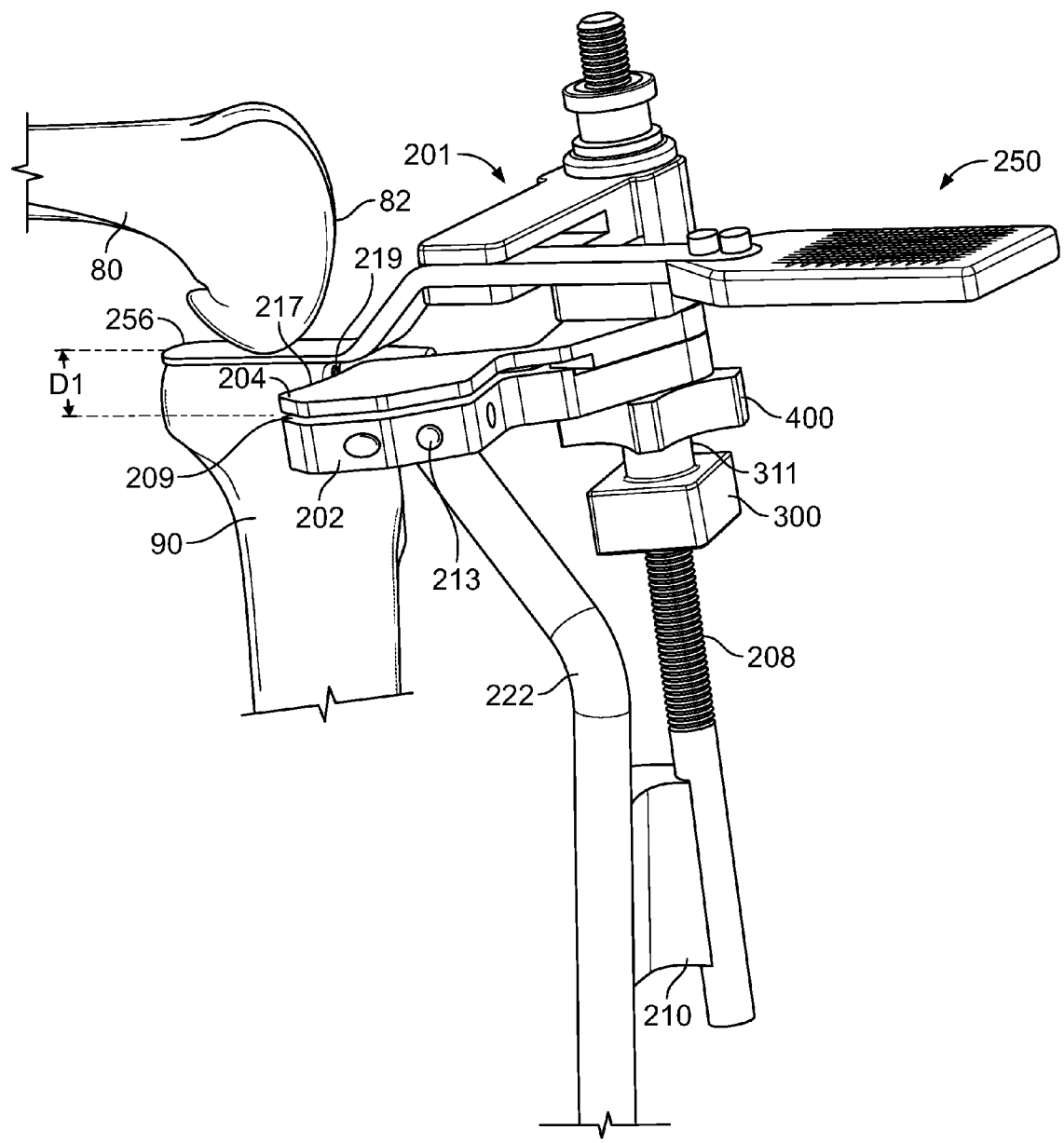
FIG. 2 is an environmental perspective view of the tibial resection guide of FIG. 1, positioned relative to a knee in flexion.
Figure 3:
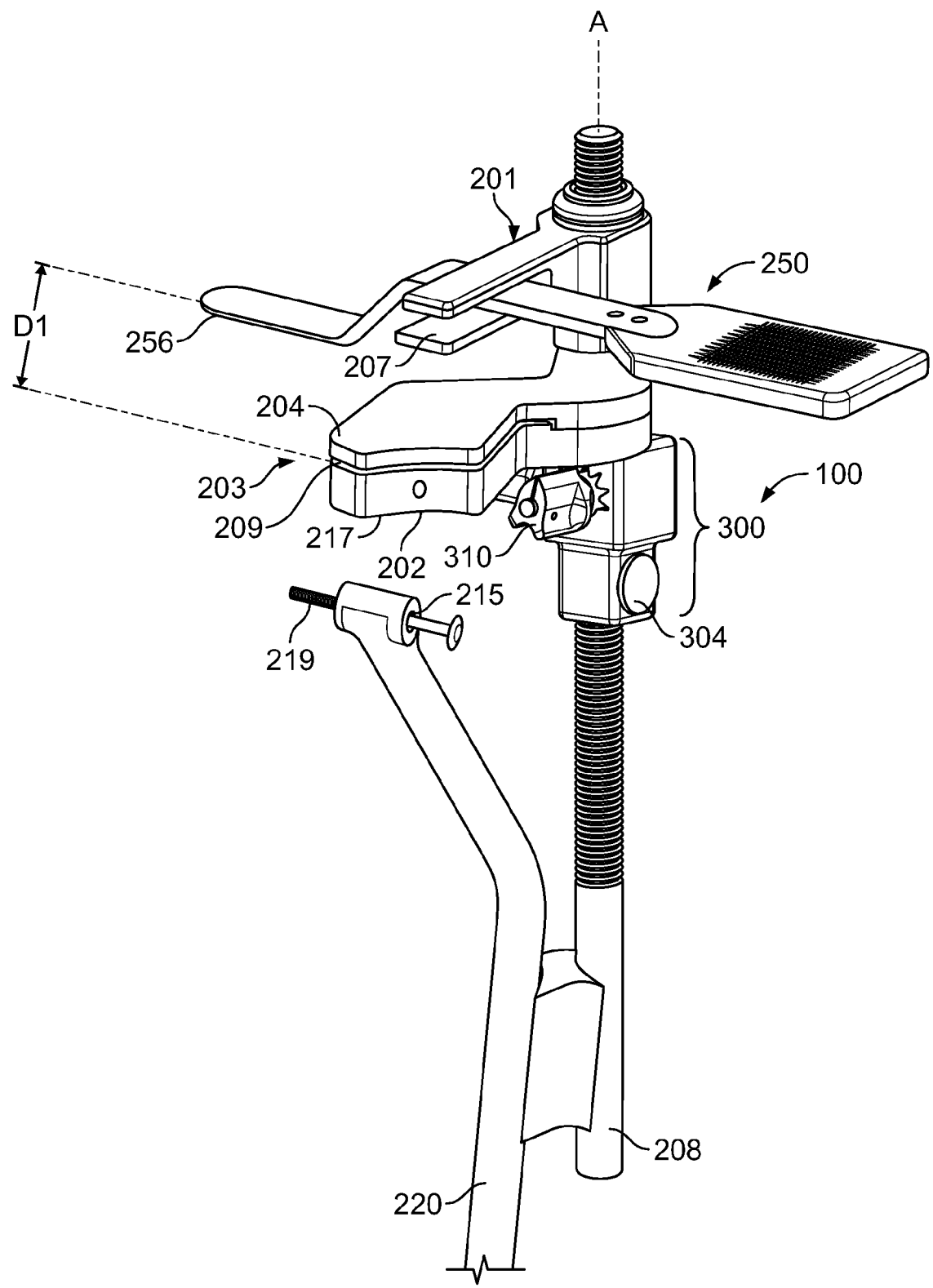
FIG. 3 is a perspective view of a tibial resection guide according to the present teachings.
Figure 3A:
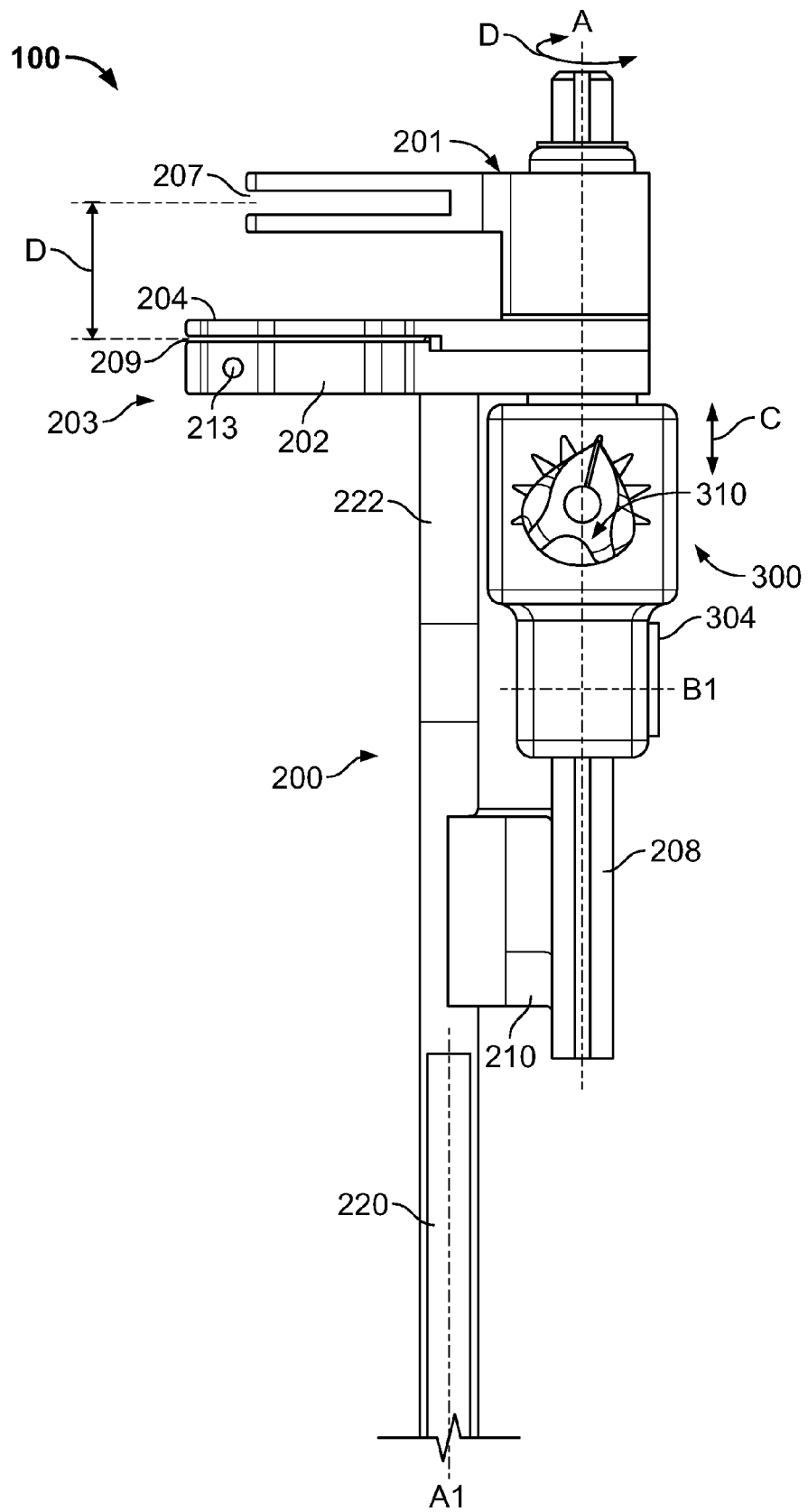
FIG. 3A is an elevational view of the tibial resection guide of FIG. 3.
Figure 5:
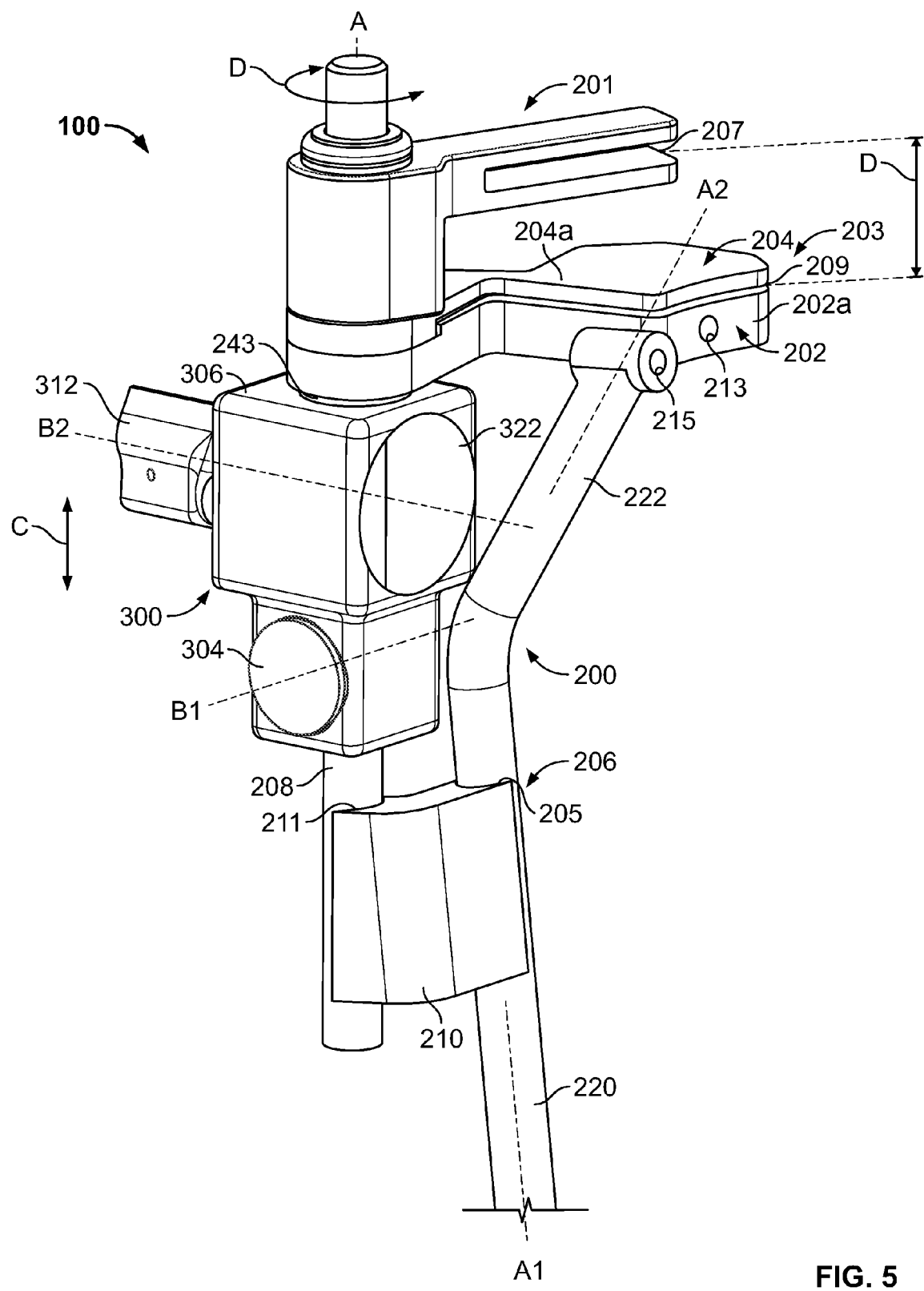
FIG. 5 is a perspective view of the tibial resection guide of FIG. 3.
Figure 7:
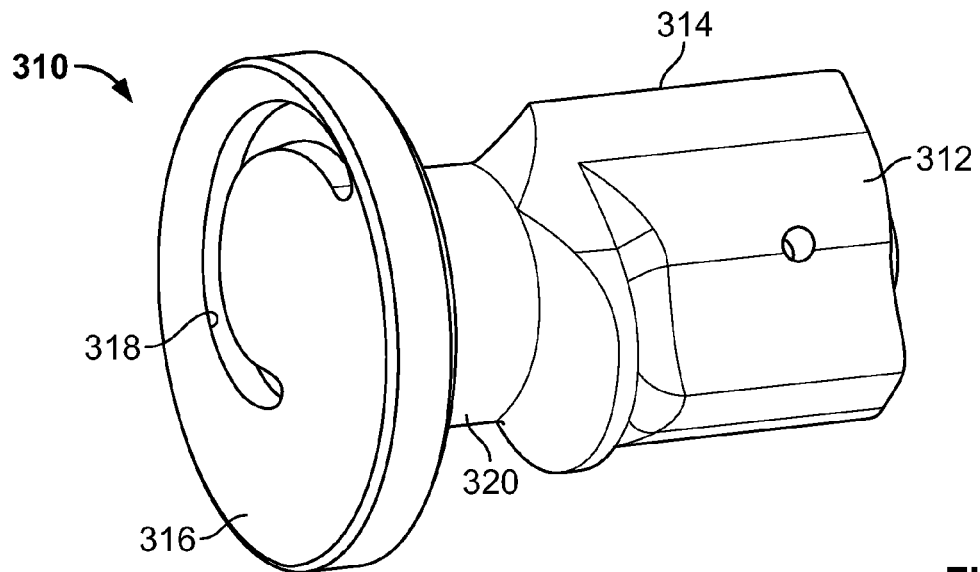
FIG. 7 is a perspective view of a first adjustment member of the tibial resection guide of FIG. 3.
Figure 8:
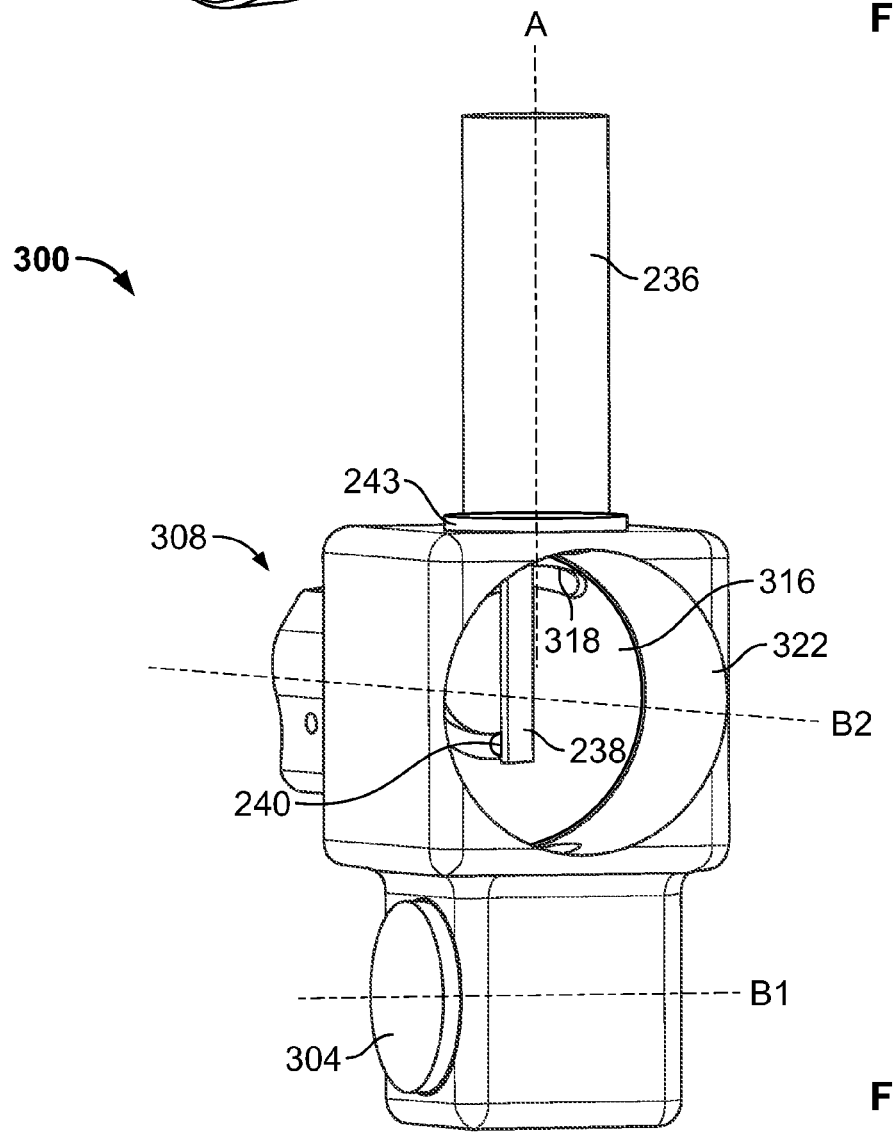
FIGS. 8 and 9 are perspective views of portions of the tibial resection guide of FIG. 3.
Figure 9:
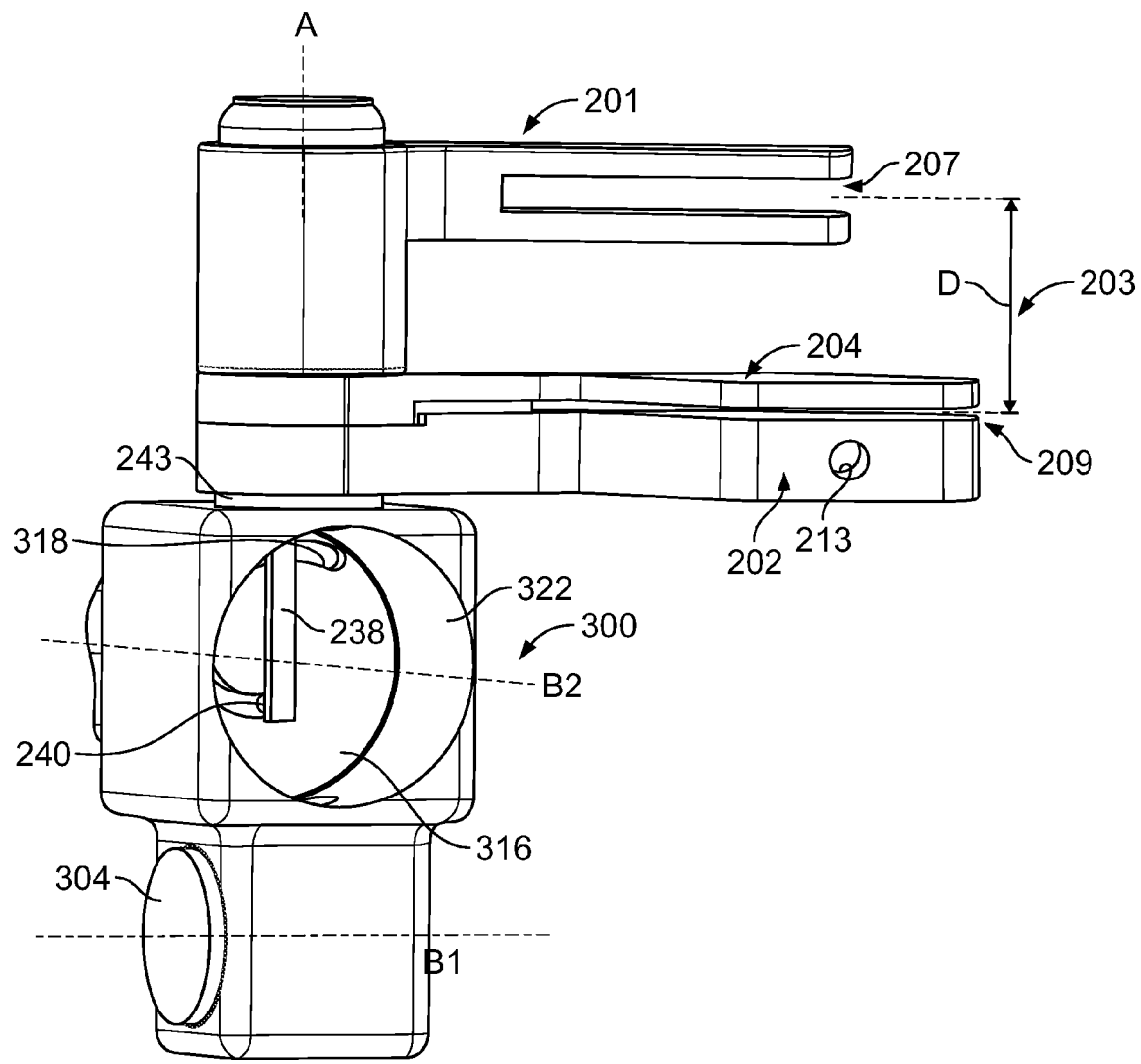

Referring to FIGS. 1, 2, 11 and 11A, an exemplary tibial resection guide 100 according to the present teachings is illustrated. Another exemplary tibial resection guide 100 according to the present teachings is illustrated in FIGS. 3, 3A and 5. The tibial resection guide 100 is shown positioned relative to a knee joint in extension in FIG. 1, and in flexion in FIG. 2.

Referring to FIGS. 3, 3A and 5, the tibial resection guide 100 can include a support member 200, a base member 300, a cutting guide 203 including a separate first guide portion 202 and a separate second guide portion 204, and a referencing guide 201 defining a referencing slot 207. The first and second guide portions 202, 204 define a single cutting slot 209 therebetween. The first guide portion 202 can include one or more fixation holes 213 for securing the first guide portion 202 to the tibia 90 with fixation pins. The cutting guide 203 can have a curved surface 217 for confirming to and engaging a corresponding tibial surface.

Figure 4:
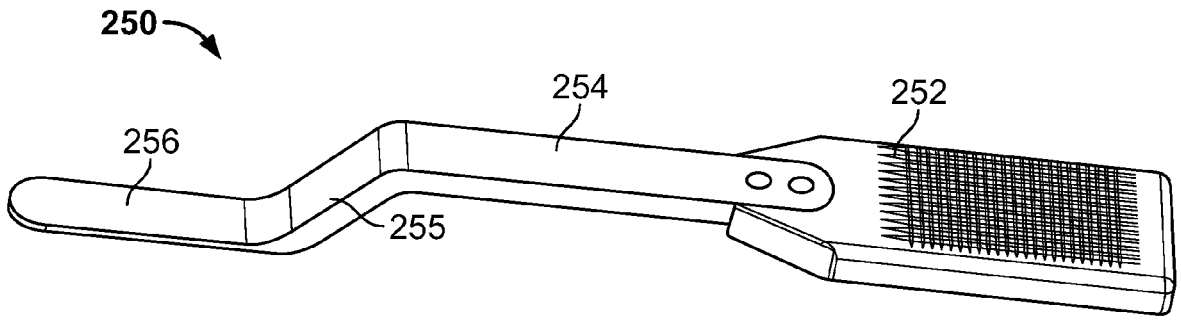
FIG. 4 is perspective view of a referencing member according to the present teachings.
Figure 15:
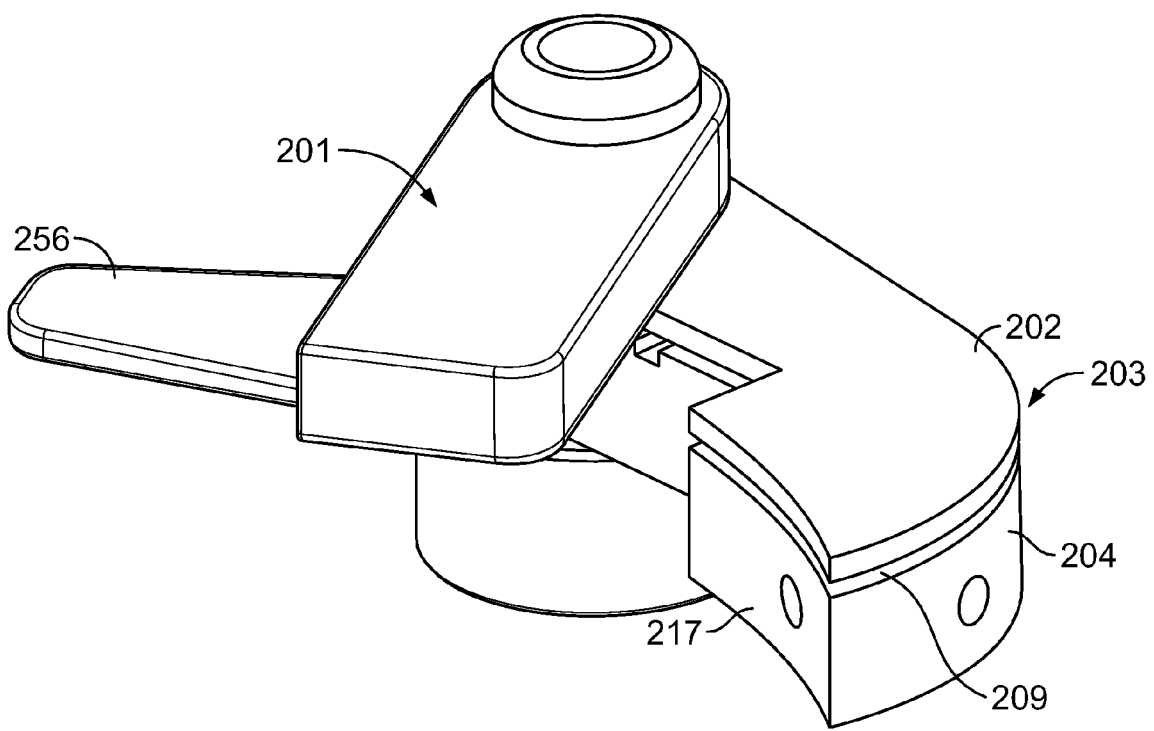
FIG. 15 is a perspective view of a portion of a tibial resection guide according to the present teachings.

An exemplary referencing member 250 that can be used with the tibial resection guide 100 and manually positioned through the referencing slot 207 is illustrated in FIG. 4. The referencing member 250 can include a holding portion 252, and an elongated Z-shaped portion that includes a bar or other shaft 254 attached to the handle portion 252 and a stylus arm 256 parallel and connected to the bar 254 at an offset thereof with an intermediate angled portion 255. The intermediate portion 255 and the stylus arm 256 are configured to nestingly receive the posterior femoral condyles 82 of a femur 80 in extension and flexion, as shown in FIGS. 1 and 2. A referencing member having a stylus 256 integrally formed as one piece with the referencing guide 201 is illustrated in FIG. 15.

Figure 13:
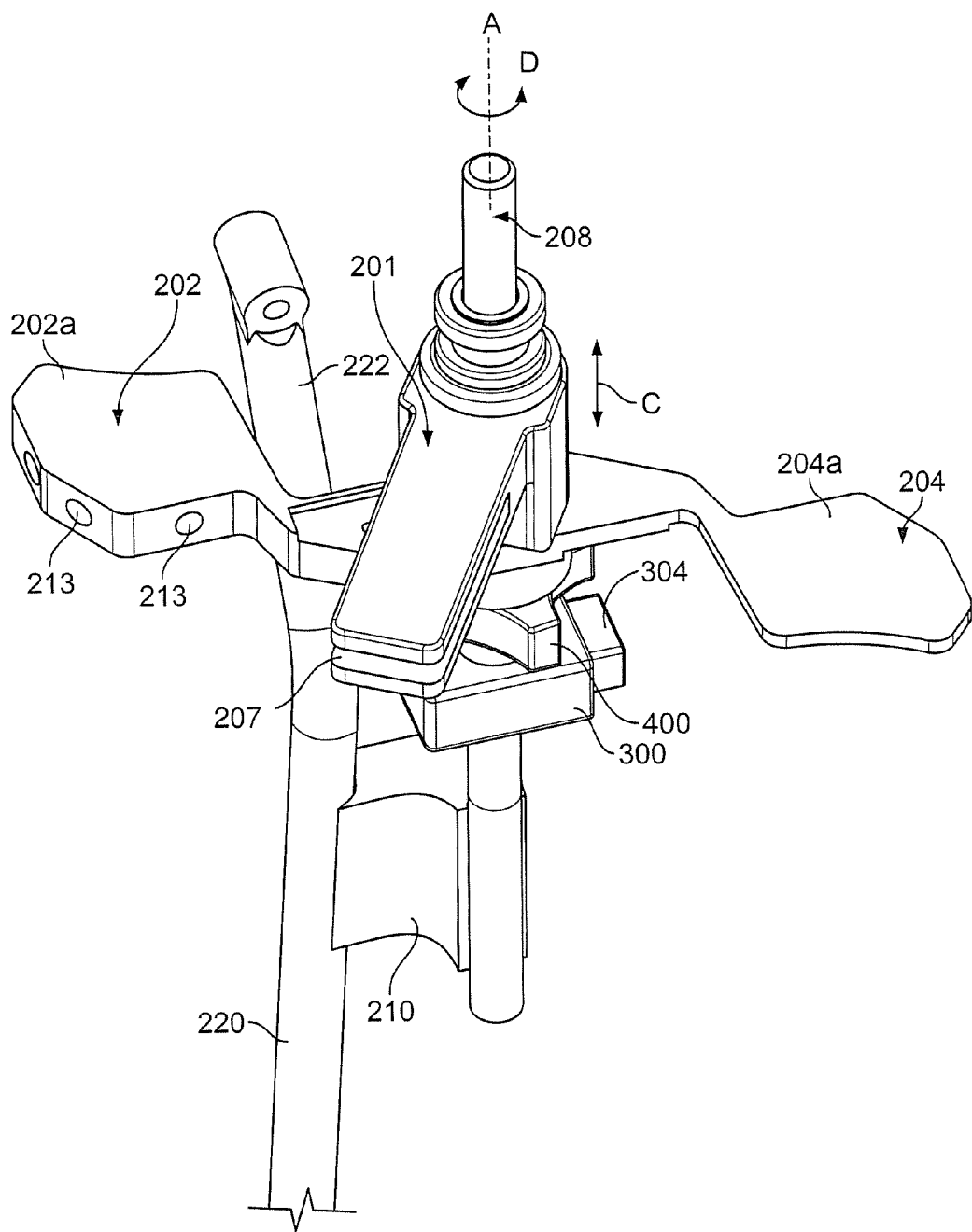
FIG. 13 is a perspective view of the tibial resection guide of FIG. 11, shown with first and second cutting members in a swung open position.
Figure 14:
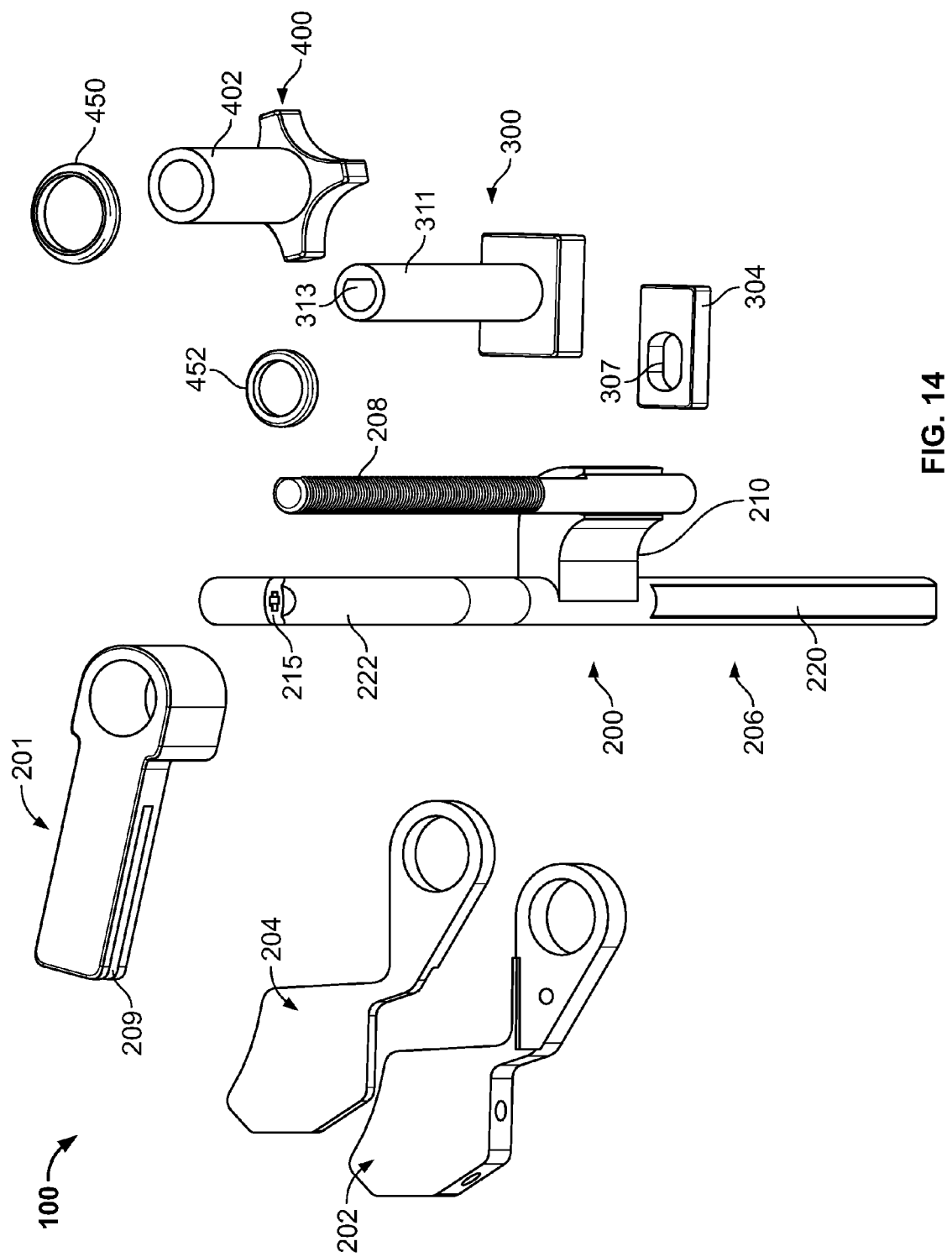
FIG. 14 is an exploded view of the tibial resection guide of FIG. 11.

The first and second guide portions 202, 204 can include corresponding first and second flanges 202a, 204a, which, when aligned over one another define the single cutting slot or opening 209 for a saw or other cutting blade or instrument. The first and second flanges 202a, 204a can be held in the aligned position over one another by a spring biased mechanism, such as a spring-biased ball and recess mechanism, for example. The first and second guide portions 202, 204 can be manually rotated relative to one another to overcome the bias, such that the flanges 202a, 204a are swung open in a position of misalignment, as shown in FIG. 13, when the guide portions 202, 204 are not used to define the cutting slot 209 for guiding a cutting blade therethrough. Optionally, the upper flange 202a of the first guide portion 202 can be used as an open cutting guide when the surgeon prefers an open cutting guide rather than a cutting slot for the cutting blade. Further, a sagittal cut can be made in the open cutting guide position. The flange 204a of the second guide portion 204 is not configured to and cannot be used by itself as a cutting guide.

Figure 6:
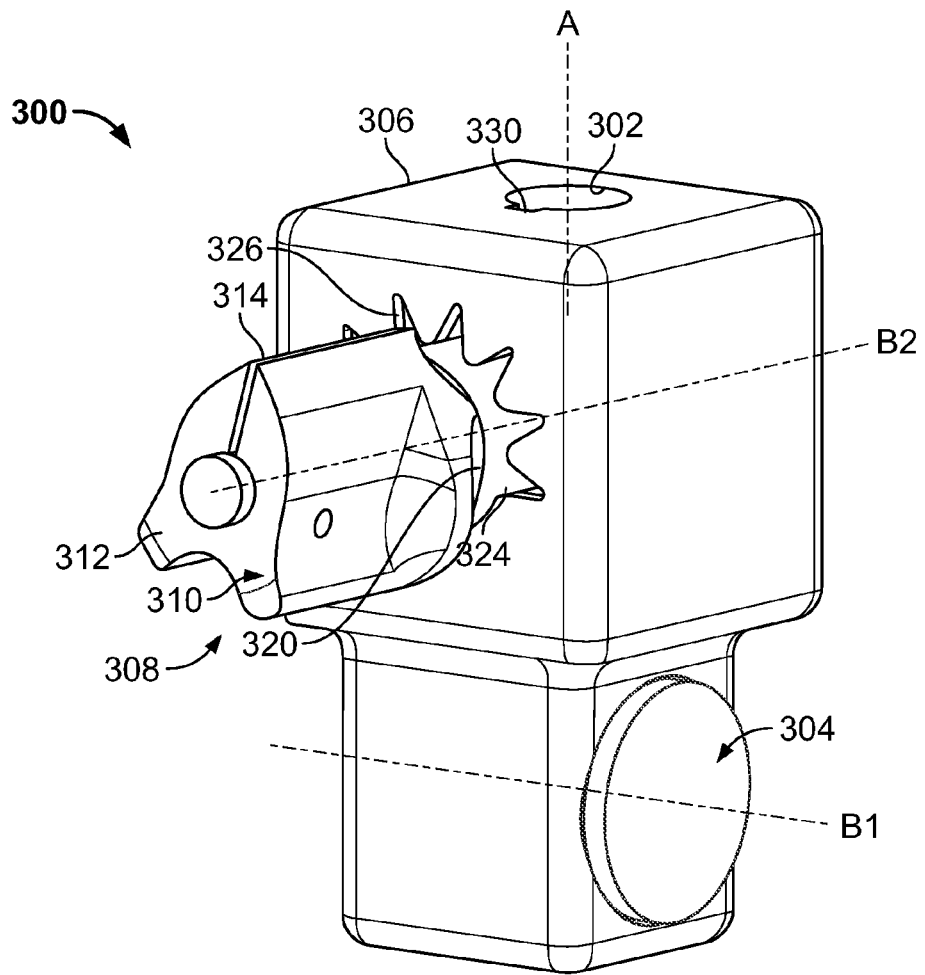
FIG. 6, is a perspective view of a base of the tibial resection guide of FIG. 3, shown with first and second adjustment members.

Referring to FIGS. 3, 5, 100 and 11A, the support member 200 can include an extramedullary alignment (EM) guide 206, an elongated supporting bar or shaft 208, and a connecting element 210. The EM alignment guide 206 and/or the shaft 208 can be removably coupled to the connecting element 210. In the exemplary illustration of FIG. 5, the EM alignment guide 206 and the shaft 208 are held in corresponding channels or slots 205, 211 defined on an outer surface of the connecting element 210. The shaft 208 has a longitudinal axis A. The EM alignment guide 206 can include a substantially straight first portion 220 having an axis A1 substantially parallel to the axis A, and a second portion 222 at an angle to the first portion 220 and oriented along an axis A2. The angle between the axes A and A1 can be made adjustable by allowing angulation of pivoting of the EM alignment guide 206 relative to the shaft 208, in a range of about 0-15 degrees, for example. The second portion 222 of the EM alignment guide 206 can include one or more fixation bores or other openings 215 for securing the EM alignment guide 206 to the tibia 90 with fixation screws or pins 219. The base member 300 can define a longitudinal bore 302 through which the base member 300 can be slidably mounted on the shaft 208, as shown in FIGS. 5 and 6. The longitudinal bore 302 can include a cutout 330 keyed to the shaft 208 to prevent rotation of the base member 300 about the shaft 208.

Gross sliding movement of the base member 300 along the shaft 208 in the direction of axis A can be controlled with a first gross or macro-adjustment member 304. The first adjustment member 304 can be a pin, a set screw, a button, or spring plunger received in a transverse bore of the base member 300 along an axis B1 and selectively be engaged or disengaged to the shaft 208. Specifically, the first adjustment member 304 can move between a first or engagement position in which the first adjustment member 304 engages the shaft 208 and prevents sliding of the base member 300 along the shaft 208, and a second or disengagement position in which the first adjustment member 304 does not engage the shaft 208 and allows the base member 300 to slide along the shaft 208 in the direction of a double arrow C. In this respect, the first adjustment member 304 can control the gross or macro-adjustment motion of base member 300. As discussed below in reference to FIGS. 11-13, the first adjustment member 304 can be a push button, which can be spring-biased to a position of engagement with the shaft 208, preventing sliding motion along the shaft 208. Depressing the button 304 can disengage the button 304 from the shaft 208 and allow sliding motion along the shaft 208.

Referring to FIGS. 5-10, the base member 300 can include a second micro-adjustment mechanism 308 that can control smaller scale or micro-adjustment movement of the base member 300 along the shaft 208. The second adjustment mechanism 308 can include a rotatable actuator 310 having a knob 312 with an indicator 314 and a disk 316. The disk 316 can be attached to the knob 312 with a neck portion 320. The disk 316 can include a curved groove defining a cam 318. The disk 316 can be received in a transverse bore 322 defined through the base member 300 along a transverse axis B2, which can be substantially orthogonal to the axes A and B1, as shown in FIG. 5. An alternative micro-adjustment mechanism is discussed below in reference to FIGS. 11-14. It is also noted that the micro-adjustment mechanism can be used with the stylus arm 256 of the referencing member 250 in position under the posterior femoral condyles 82, and can provide the surgeon a sense of the tension in the medial collateral ligament.

Referring to FIG. 6, the neck portion 320 of the knob 312 can pass through an opening 324 of the base member 300 that communicates with the transverse bore 322. The opening 324 can define discrete angular positions 326, such that the knob 312 can be rotated incrementally about the axis B2. Rotation of the knob 312 such that the indicator 314 of the knob moves from a first position 326 to an immediately adjacent position 326, corresponds to one unit of rotation, which is converted by the second adjustment mechanism 308 to one unit of axial motion along the shaft 208 in the direction of the longitudinal axis A, as discussed below. The unit of linear micro-adjustability can be about one millimeter, for example.

Figure 10:
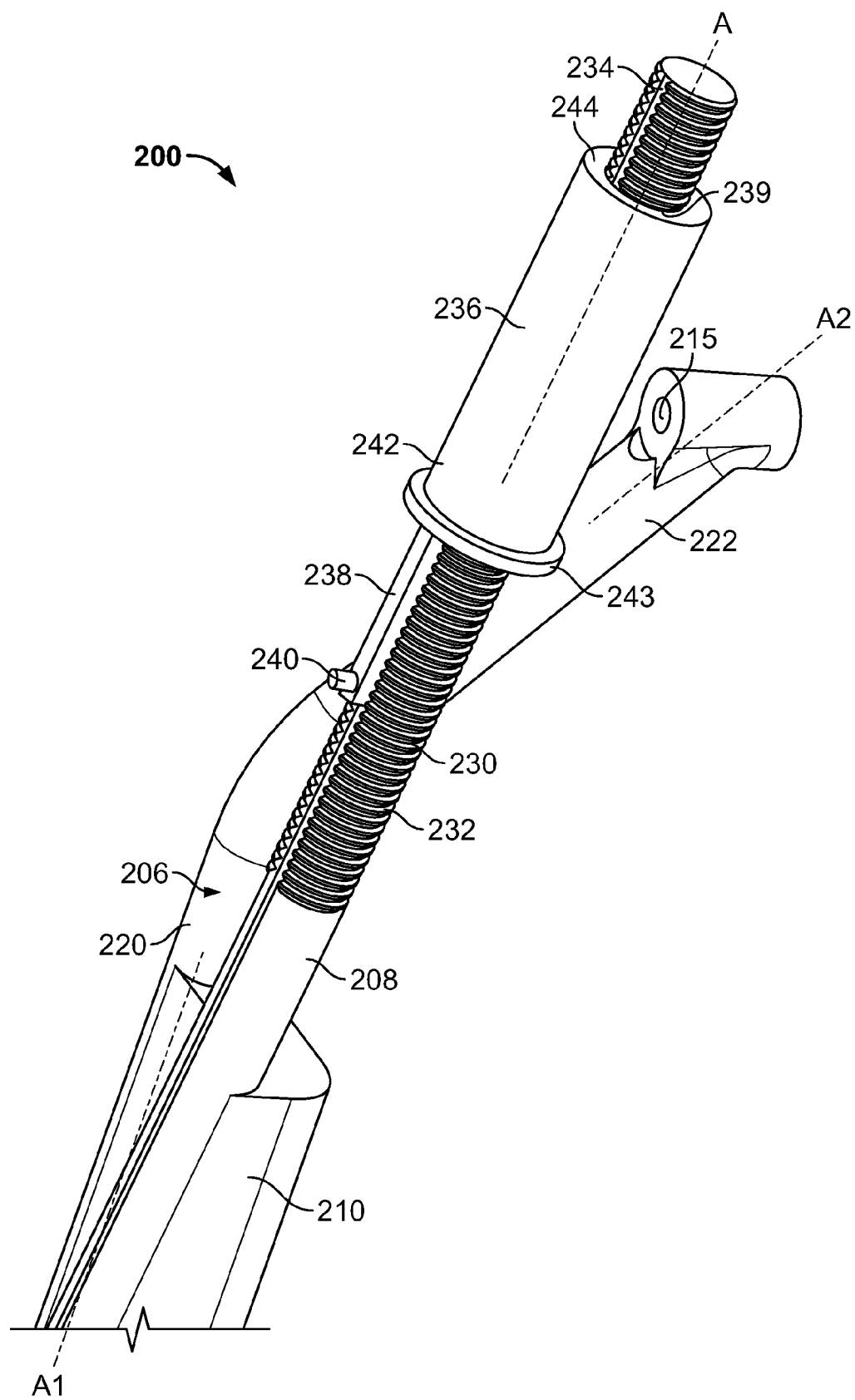
FIG. 10 is a perspective view of a portion of an adjustment member of the tibial resection guide of FIG. 3.

Referring to FIGS. 7-10, the shaft 208 can include a threaded portion 230 with threads 232 and a longitudinal groove or slot or other thread interruption 234 interrupting the circumference of the threads 232, as shown in FIG. 10. A sleeve 236, having a longitudinal bore 239 and first and second ends 242, 244, can be placed over a portion of the threaded portion 230 of the shaft 208. An annular flange 243 can be formed adjacent the first end 242 of the sleeve 236 and positioned on an upper first surface 306 of the base member 300. The sleeve 236 can include a longitudinal extension 238 extending from the first end 242 of the sleeve 236 into the longitudinal bore 302 of the base member 300. A short pin or post 240 can be perpendicularly attached to the other end of the extension 238 inside the bore 302. The pin 240 can be received in the curved groove 318 of the disk 316. Rotating the knob 312 can rotate the curved groove 318 causing the pin 240 to move along the axis A. As the pin 240 moves linearly along the axis A, the extension 238 moves along the groove 234 and sleeve moves linearly along the axis A.

Referring to FIG. 5, each of the first guide portion 202, the second guide portion 204, and the referencing guide 201 is rotatably mounted on the shaft 208, such that each of the first guide portion 202, the second guide portion 204, and the referencing guide 201 can freely and independently swivel, swing or rotate about the axis A in the directions indicated by the curved arrow D. The first guide portion 202, the second guide portion 204, and the referencing guide 201 can be stacked on one another on the flange 243 of the sleeve 238 over the first surface 306 of the base member 300. Accordingly, rotating the knob 312 over one angular increment moves the first guide portion 202, the second guide portion 204, and the referencing guide 201 one axial increment along the axis A as one body, without changing their relative positions. In particular, the distance D between the referencing slot 207 and the cutting slot 209 remains constant during motion along the axis A. Further, when the referencing member 250 is inserted through the referencing slot 207, the distance D1 between the stylus arm 256 and the cutting slot 209 remains constant during motion along the axis A. In this respect, the shaft 254 of the referencing member 250 is held snugly by the referencing slot 207, such that the referencing arm 256 is held substantially perpendicularly to the axis A. Keeping the distances D and D1 fixed can help avoid inadvertent changes of referencing level and free the surgeon from concern over any such inadvertent changes.

Similarly, disengaging the gross adjustment member 304 from engagement to the shaft 208 allows gross sliding of the base member 300 along the axis A and simultaneous concomitant sliding of the first guide portion 202, the second guide portion 204, and the referencing guide 201 without any change in the distances between these guides. Specifically, the distance D between the referencing slot 207 and cutting slot 209 remains constant during any adjustment of the tibial resection guide 100, either by gross adjustment using the first adjustment member 304 or by micro-adjustment using the incremental adjustment knob 312, as shown in FIG. 5.

Referring to FIGS. 11-14, an alternative micro-adjustment mechanism in the form of a rotatable knob or nut 400 having a sleeve 402 with internal threading and threadably coupled to the threaded portion 230 of the shaft 208 can be used instead of the micro-adjustment mechanism 308 illustrated in FIGS. 5-9. Rotating the nut 400 moves the nut 400 along the shaft 208, thereby moving the cutting guide 203 and the referencing guide 201 along the axis A without changing the distance D between the cutting slot 209 and the referencing slot 207, as discussed above in connection with FIGS. 5-9. Washers 450, 452 can be placed over the shaft 208 above the referencing guide 201 preventing relative movement of the referencing guide 201 and the cutting guide 203.

Figure 12:
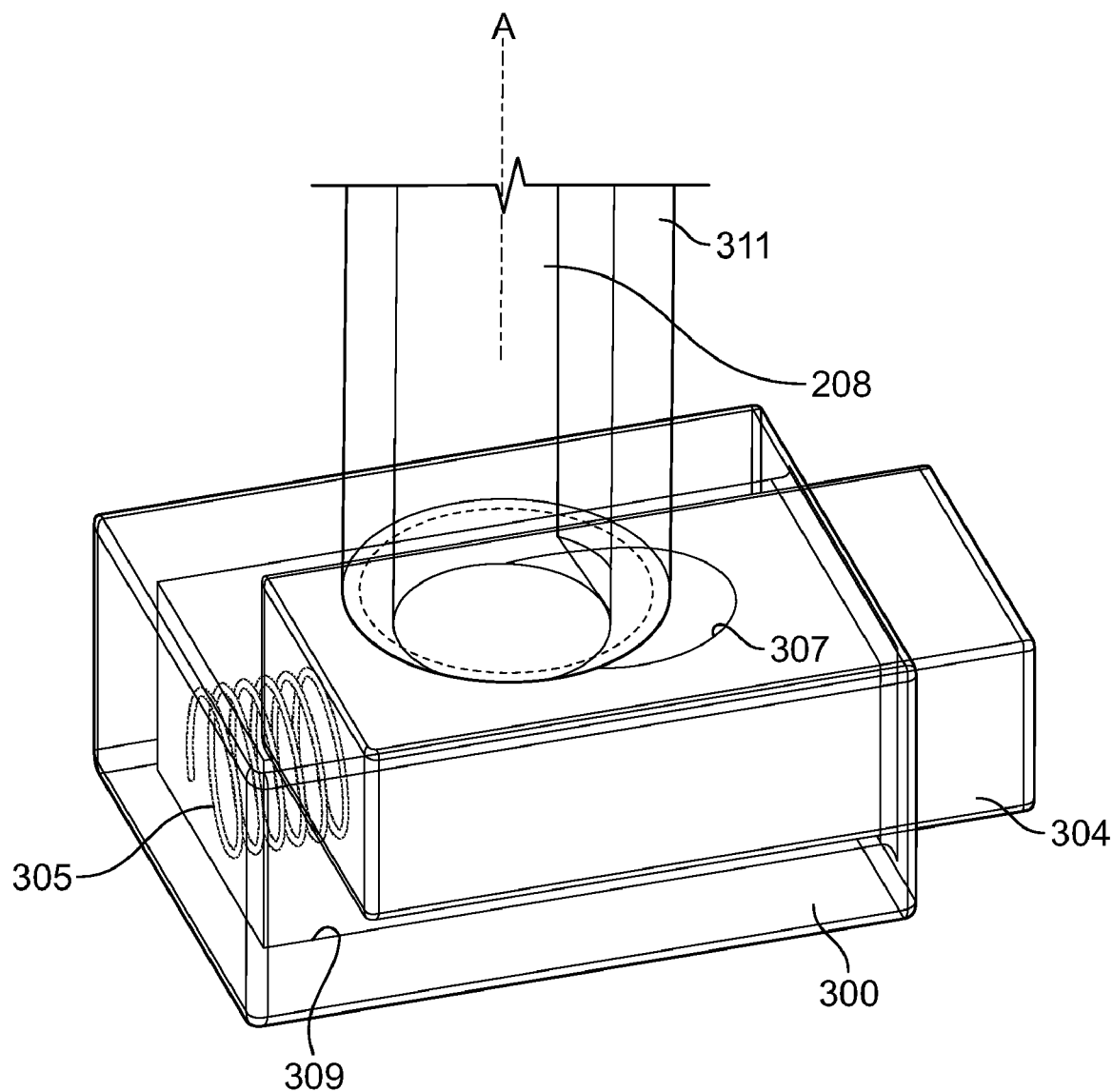
FIG. 12 is a perspective view of a macro-adjustment member of the tibial resection guide of FIG. 11.

Referring to FIG. 12, an exemplary macro-adjustment mechanism is illustrated. The first adjustment member is in the form of push button 304 slidably received in a cavity 309 of a base member 300, which, in this aspect, includes a tubular portion 311 having a longitudinal bore 313 with a D-shaped or other keyed cross-section, through which the shaft 208 can pass and move slidably but not rotatably. The button 304 defines a corresponding elongated open bore 307, through which the shaft 208 can pass. A spring or other biasing element 305 biases the wall of the opening 307 against the shaft 208 preventing sliding along the axis A. Depressing the button 304, compresses the spring 305, disengages the shaft 208 from the open bore 307, and allows sliding along the axis A.

Referring to FIGS. 1 and 2, the tibial resection guide 100 can be positioned adjacent to the knee joint in extension and/or flexion, as shown, for determining the tibial resection level. The tibial resection guide 100 can be attached to the tibia 90 using the EM alignment guide 206. Although the tibial resection guide of FIG. 11A is shown in FIGS. 1 and 2, it will be appreciated that the tibial resection guide 100 of FIG. 3 can be similarly attached to the tibia 90. The referencing member 250 can be manually inserted through the referencing slot 207 such that the stylus arm 256 is approximately in position for referencing the posterior condyles of the femur.

Figure 11:
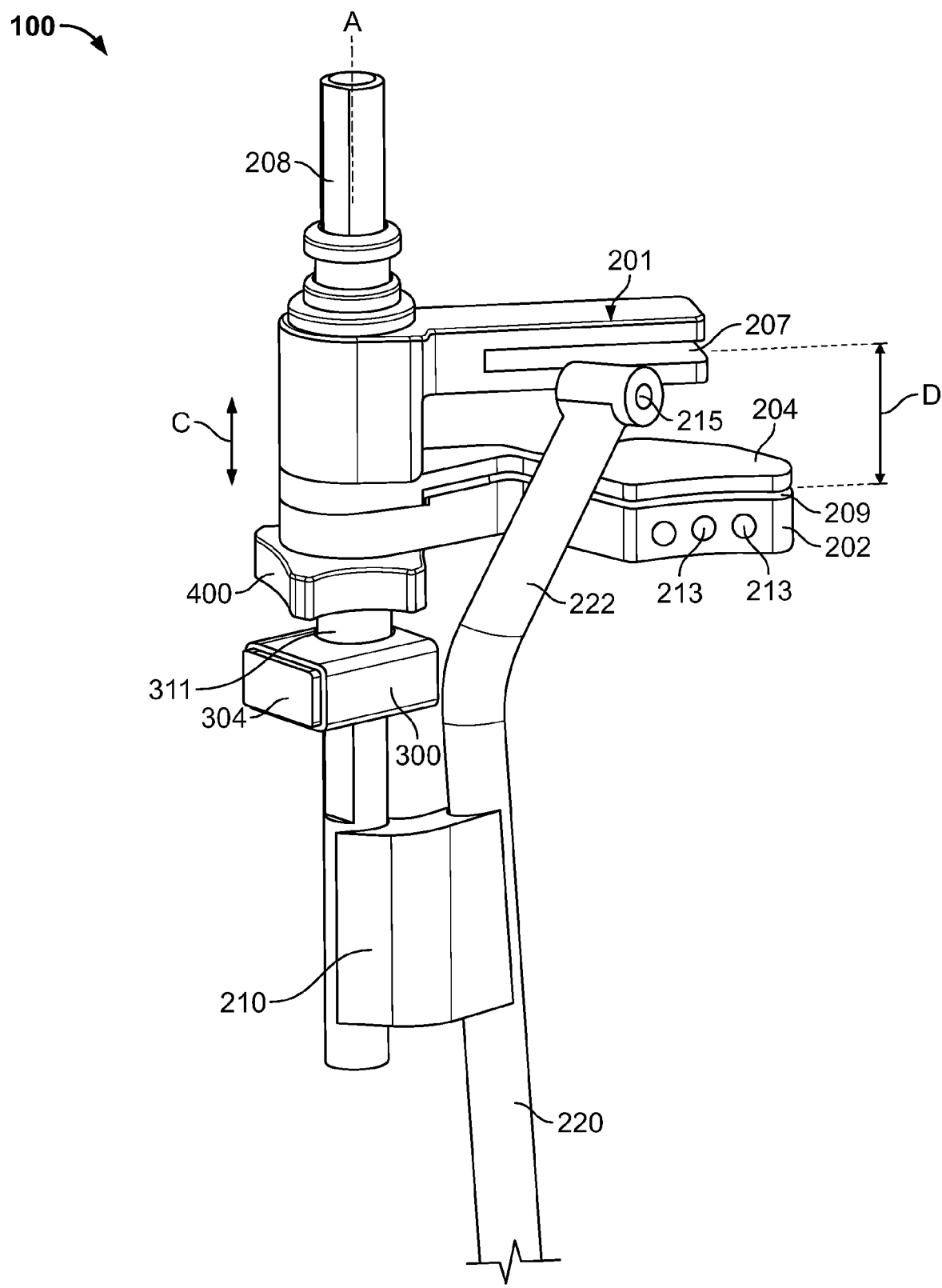
FIG. 11 is perspective view of a tibial resection guide according to the present teachings.
Figure 11A:
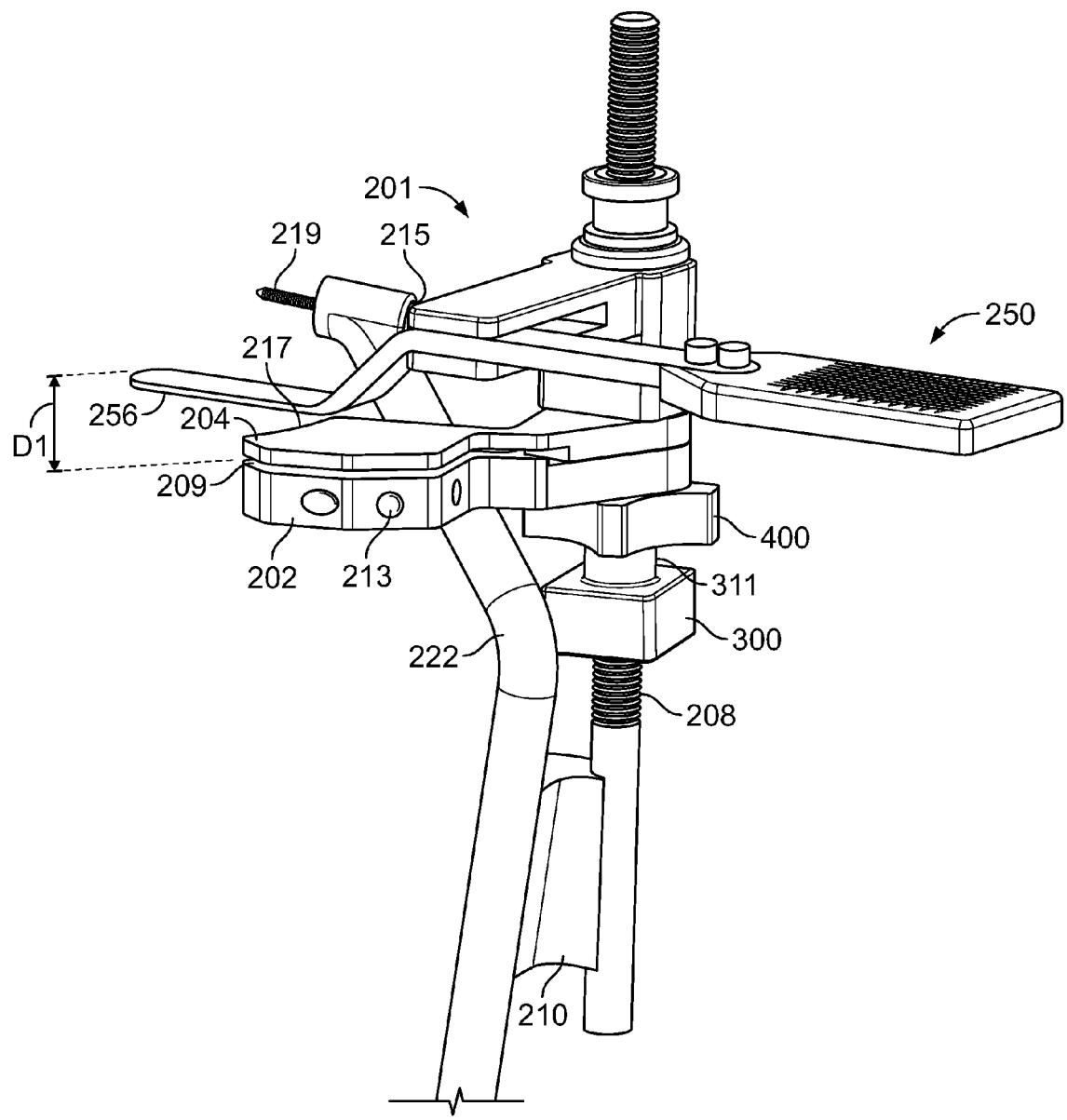
FIG. 11A is another perspective view of the tibial resection guide of FIG. 11.

The stylus arm 256 can be brought in contact with the posterior condyles first by a gross adjustment using the first adjustment member 304 to slide the base member 300 along the axis A, and then by micro-adjustment using the rotatable knob 312 shown in FIG. 5 or the rotatable nut 400 shown in FIGS. 11 and 11A to incrementally move the first and second guide portions 202, 204 and the referencing guide 201 along the axis A until the stylus arm 256 of the referencing member 250 can contact the posterior femoral condyles 82 when inserted through the referencing slot 207. As discussed above, during this movement the distance D between the referencing slot 207 and the cutting slot 209 remains constant and unchanged. The first and second guide portions 202, 204 can be rotated away from the tibia 90 during the measurement procedure, and then rotated back toward the tibia 90 for the resection procedures. The first guide portion 202 can be secured to the tibia 90 with fixation pins or other fasteners passing through the fixation holes 213. The resection level can be measured using a length scale associated with angular positions 326 of the rotatable knob 312 of FIG. 5, as discussed above, or with a scale associated with the rotatable nut 400 of FIG. 11. The referencing guide 201 can also be swiveled about the shaft 208 in and out of the referencing position, to facilitate corresponding resection measurement and resection procedures.

It will be appreciated that the tibial resection guide 100 of the present teachings provides various degrees of gross and micro-adjustability in a linear direction for determining the resection level, as well as independent swiveling motions of the referencing guide 201 and the first and second guide portions 202, 204, to enable the surgeon to use the cutting slot in an unobstructed manner and to easily visualize the resection area.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A tibial resection guide for a knee joint comprising:
   a support member including a longitudinal shaft;
   a femoral referencing guide rotatably mounted on the longitudinal shaft and configured for referencing a femur of the knee joint, the referencing guide including a referencing slot;
   a femoral referencing member having a stylus arm attached to a bar, the stylus arm configured for referencing a posterior condyle of a femur of the knee joint and the bar removably passing through the referencing slot;
   a cutting guide rotatably coupled to the longitudinal shaft, the cutting guide defining a cutting slot, the cutting slot positioned at a fixed distance from the referencing slot; and
   an adjustment mechanism operable to move the referencing guide and the cutting guide along the longitudinal shaft without changing the fixed distance.

2. The tibial resection guide of claim 1, wherein the stylus arm is parallel and attached to the bar at an offset with an intermediate angled portion.

3. The tibial resection guide of claim 1, wherein the referencing guide and the referencing slot are rotatable relative to the cutting slot.

4. The tibial resection guide of claim 1, further comprising a base member supporting the cutting guide and having a bore and slidably mounted over the longitudinal shaft through the bore.

5. The tibial resection guide of claim 1, wherein the cutting guide includes first and second separable flanges, each of the first and second flanges independently rotatable about the longitudinal shaft between a first position in which the first and second flanges are aligned over one another and define the cutting slot therebetween and a second in which the first and second flanges are not aligned over one another.

6. The tibial resection guide of claim 4, wherein the adjustment mechanism includes a macro-adjustment mechanism movable between a first position preventing sliding of the base along the longitudinal shaft and a second position of allowing sliding of the base member along the longitudinal shaft.

7. The tibial resection guide of claim 6, wherein the macro-adjustment mechanism includes a push button, the push button spring-biased to the first position preventing movement along the longitudinal shaft.

8. The tibial resection guide of claim 6, further comprising a micro-adjustment mechanism that includes a nut threadably coupled to a threaded portion of the longitudinal shaft.

9. The tibial resection guide of claim 6, further comprising a micro-adjustment mechanism that includes a rotatable actuator having a curved groove defining a cam and a pin received in the curved groove configured for moving the base member along the longitudinal axis in smaller increments than the macroadjustment mechanism.

10. A tibial resection guide for a knee joint comprising:
a support member including a longitudinal shaft;
a femoral referencing guide rotatably mounted on the longitudinal shaft and configured for referencing a femur of the knee joint, the referencing guide including a referencing slot, the referencing guide independently rotatable about the longitudinal shaft;
a first guide portion having a first flange, the first guide portion coupled to the longitudinal shaft and independently rotatable about the longitudinal shaft;
a second guide portion having a second flange, the second guide portion coupled to the longitudinal shaft and independently rotatable about the longitudinal shaft, the first and second flanges rotatable between a first position of stacked alignment in which the first and second flanges are aligned over one another and define a cutting slot therebetween, and a second position in which the first and second flanges are out of stacked alignment, and wherein the first and second guide portions positioned under the referencing guide along the longitudinal shaft;
a base member movably supported on the longitudinal shaft and positioned under the first and second guide portions; and
an adjustment mechanism configured to move the referencing guide and the first and second guide portions along the longitudinal shaft by moving the base member along the longitudinal shaft.

11. A tibial resection guide of claim 10, wherein the longitudinal shaft passes through a bore of the base member, the bore keyed to the longitudinal shaft and preventing rotation of the base member relative to the longitudinal shaft.

12. The tibial resection guide of claim 11, wherein the referencing slot and the cutting slot define a fixed distance therebetween, the fixed distance remaining constant during the movement of the referencing guide and the first and second guide portions along the longitudinal shaft.

13. The tibial resection guide of claim 10, further comprising a separate referencing member, the referencing member manually insertable through the referencing slot for referencing posterior condyles of a femur of the knee joint.

14. The tibial resection guide of claim 10, wherein the adjustment mechanism includes a macro-adjustment mechanism and a micro-adjustment mechanism.

15. The tibial resection guide of claim 14, wherein the macro-adjustment mechanism includes a push button, the push button spring-biased to a position preventing sliding movement of the base member along the longitudinal shaft.

16. The tibial resection guide of claim 14, wherein the micro-adjustment mechanism includes a nut threadably coupled to a threaded portion of the longitudinal shaft.

17. The tibial resection guide of claim 14, wherein the micro-adjustment mechanism includes a rotatable actuator having a curved groove defining a cam and a pin received in the curved groove configured for moving the base member along the longitudinal axis in smaller increments than the macroadjustment mechanism.

18. A tibial resection guide for a knee joint comprising:
a support member including a longitudinal shaft;
a referencing guide mounted on the longitudinal shaft, the referencing guide integrally forming a stylus arm configured for engaging posterior femoral condyles of a femur of the knee joint;
a cutting guide coupled to the longitudinal shaft, the cutting guide positioned under the referencing guide and including first and second flanges independently rotatable relative to the longitudinal shaft between a first position of stacked alignment in which the first and second flanges are aligned over one another and define a cutting slot therebetween, and a second position in which the first and second flanges are out of stacked alignment, the first and second guide positioned are positioned under the referencing guide along the longitudinal axis, the cutting slot positioned at a fixed distance from the stylus arm;
a base member movably supported on the longitudinal shaft and positioned under the first and second flanges; and
an adjustment mechanism configured to move the referencing guide and the cutting guide along the longitudinal shaft without changing the fixed distance by moving the base member along the longitudinal shaft.

19. The tibial resection guide of claim 18, wherein the referencing guide is rotatable about the longitudinal shaft independently from the cutting guide.

20. The tibial resection guide of claim 18, wherein the adjustment mechanism includes a macro-adjustment mechanism movable between a first position preventing sliding of the base member along the longitudinal shaft and a second position of allowing sliding of the base member along the longitudinal shaft.

* * * * *